(12) United States Patent
Chang et al.

(10) Patent No.: US 8,833,136 B2
(45) Date of Patent: Sep. 16, 2014

(54) ROTARY-DRUM HYDRAULIC-IMPACT ABRASION TESTING MACHINE

(75) Inventors: Ta-Peng Chang, Taipei (TW); Chih-Yen Lin, Taipei (TW); Kuo-Hua Lee, New Taipei (TW); Tzong-Ruey Yang, Taipei (TW)

(73) Assignee: National Taiwan University of Science and Technology, Taipei (TW)

( * ) Notice: Subject to any disclaimer, the term of this patent is extended or adjusted under 35 U.S.C. 154(b) by 345 days.

(21) Appl. No.: 13/529,013

(22) Filed: Jun. 21, 2012

(65) Prior Publication Data

US 2013/0327120 A1     Dec. 12, 2013

(30) Foreign Application Priority Data

Jun. 6, 2012    (TW) .............................. 101120282 A

(51) Int. Cl.
     *G01N 3/56*         (2006.01)
(52) U.S. Cl.
     USPC .................................................................. 73/7
(58) Field of Classification Search
     CPC .......... G01N 3/56; G01N 3/565; G01N 3/567
     USPC ................................................................. 73/7
     See application file for complete search history.

(56) References Cited

U.S. PATENT DOCUMENTS 4,583,392 A *   4/1986   Holmgren et al. .................. 73/7

FOREIGN PATENT DOCUMENTS

JP          2005283416 A *   10/2005         G01N 3/56

* cited by examiner

*Primary Examiner* — Hezron E Williams
*Assistant Examiner* — Nathaniel Kolb

(57) ABSTRACT

The present invention relates to a rotary-drum hydraulic-impact abrasion testing machine, which is used to process an abrasion test and a damage simulation for a plurality of hydraulics structures and comprises: a rotary-drum supporting framework, a rotary-drum and a plurality of sample fixing assembly. The sample fixing assembly at least comprises a housing, a first spacer and a plurality of first studs. In which, there are a plurality of sample openings formed on the side wall of the rotary-drum for respectively accommodating the hydraulics structure samples, and each sample opening is disposed with a long blocking plate and a short blocking plate on the two sides thereof. In the present invention, the rotary-drum hydraulic-impact abrasion testing machine is used to simultaneously execute the abrasion test and the damage simulation for multi hydraulics structures precisely.

10 Claims, 6 Drawing Sheets

ROTARY-DRUM HYDRAULIC-IMPACT ABRASION TESTING MACHINE

BACKGROUND OF THE INVENTION

1. Technical Field

The present invention relates to an impact abrasion testing machine for concrete hydraulics structures, and more particularly, to a rotary-drum hydraulic-impact abrasion testing machine.

2. Description of Related Art

Because there are many steep hillsides in Taiwan, the concrete hydraulics structures, such as spillways or sluiceways, are subject to attack, abrasion and erosion of torrent carried with gravel, cobbles and boulders caused by heavy rain or typhoon; that causes severe damage such as the delaminating of the surface and the exposure of the primary steel frame of the spillways or sluiceways, and then shortens the service time of those concrete hydraulics structures eventually.

According to the classification of ACI 210R-93, the erosions on the hydraulics structures include: cavitation erosion, abrasion erosion and chemical erosion. More clearly, scholars David Plum and Fang Xufei divide the erosions on the hydraulics structures to abrasive wear, solid particles erosion, abrasion caused by sharp edges of solid particles, and pre-erosion peeling. After understanding the various erosions on the hydraulics structures, the most important thing is how to carry out the optimization design for the hydraulics structures. In which, scholar Papenfus finds that the major factor for wear resistance of the hydraulics structures is the binding between hardness, aggregate and cement mortar of a concrete hydraulics structure. Thereafter, for increasing the wear resistance of the concrete hydraulics structure, both novice researchers and scholars make great efforts to study how to find an optimal mixing proportion for the hardness, the aggregate and the cement mortar of the concrete hydraulics structure.

Inheriting to above descriptions, when studying the optimal mixing proportion for the hardness, the aggregate and the cement mortar, the researchers must do a verification for that through abrasion testing, therefore the researchers are able to confirm the relationship between the mixing proportion of the hardness, the aggregate and the cement mortar and the wear resistance of the concrete hydraulics structure. According to the material testing methods provided by American Society for Testing Materials (ASTM), the abrasion testing methods for the concrete hydraulics structure include: sand blasting testing of C418, C779 testing method for abrasion resistance of horizontal concrete surfaces, rotational grinding testing of C994, and abrasion testing of C1138.

The abrasion testing ways of C418, C779 and C994 are all belong to dry abrasion testing way; However, because the surface layers of the hydraulics structures are always subject to grinding, scraping, cutting, rubbing, scouring, and impacting by the torrent carried with the gravel, the cobbles and the boulders, the erosions on the surface layers of the hydraulics structures are very complex. So that, the researchers commonly use the C1138 abrasion testing way to verify and simulate the erosions on the surface layers of the hydraulics structures caused by the colloids in water.

Please refer to FIG. 1, there is shown a cross-sectional view of a conventional C1138 abrasion testing machine. As shown in FIG. 1, the C1138 abrasion testing machine 1' includes: a base 11' and a barrel 12', wherein the bottom of the barrel 12' provided with a sample supporting framework 121' bearing with a concrete sample 2'. When processing the abrasion testing, it needs to inject water into the barrel 12' and next to put a plurality of steel balls 13' with different sizes on the surface layer of the concrete sample 2'. Then, by operating a motor (not shown) to drive the shaft 14' in the barrel 12' to rotate, water current is resulted from the rotation of a plurality of mixing blade 15'. Thus, through the water current, the steel balls 13' would move on the surface layer of the concrete sample 2', so as to simulate the impact on the (concrete) hydraulics structure caused by the water containing sand.

According to above descriptions, it is able to know that the C1138 abrasion testing machine 1' is a commonly-used abrasion testing machine for the hydraulics structures, and the testing time of the C1138 abrasion testing machine 1' is at least 48 hr according to the specification of ASTM. However, when the C1138 abrasion testing machine 1' is used to process the abrasion testing for a high-strength concrete, it cannot find any obvious divergences on the surface layer of the high-strength concrete under 48 hr testing time because the surface layer of the high-strength concrete has a better wear resistance; so that, 72 hr is an appropriated testing time for the high-strength concrete. Therefore, according to above descriptions, it is able to find that long testing time is the main shortcoming of the C1138 abrasion testing machine 1'. Moreover, since the erosions on the surface layers of the hydraulics structures caused by the water containing sand are very complex, the C1138 abrasion testing machine 1' cannot completely simulate all natural erosions on the surface layers of the hydraulics structures; That is another drawback of the C1138 abrasion testing machine 1'.

Accordingly, in view of the conventional C1138 abrasion testing machine still having shortcomings and drawbacks, the inventor of the present application has made great efforts to make inventive research thereon and eventually provided a rotary-drum hydraulic-impact abrasion testing machine.

BRIEF SUMMARY OF THE INVENTION

The primary objective of the present invention is to provide a rotary-drum hydraulic-impact abrasion testing machine.

Accordingly, in order to achieve the primary objective of the present invention, the inventor proposes a rotary-drum hydraulic-impact abrasion testing machine, comprising:
a rotary-drum supporting framework;
a rotary-drum, disposed on the rotary-drum supporting framework provided with at least one sample opening for accommodating at least one hydraulics structure sample; and
at least one sample fixing assembly, used for fixing the hydraulics structure sample in the sample opening;
wherein the inner side walls of the rotary-drum is provided with a plurality of blocking plates axially-extended in parallel around each of the sample openings in the rotary-drum.

BRIEF DESCRIPTION OF THE SEVERAL VIEWS OF THE DRAWINGS

The invention as well as a preferred mode of use and advantages thereof will be best understood by referring to the following detailed description of an illustrative embodiment in conjunction with the accompanying drawings, wherein.

DETAILED DESCRIPTION OF THE INVENTION

To more clearly describe a rotary-drum hydraulic-impact abrasion testing machine according to the present invention, embodiments of the present invention will be described in detail with reference to the attached drawings hereinafter.

Figure 1:
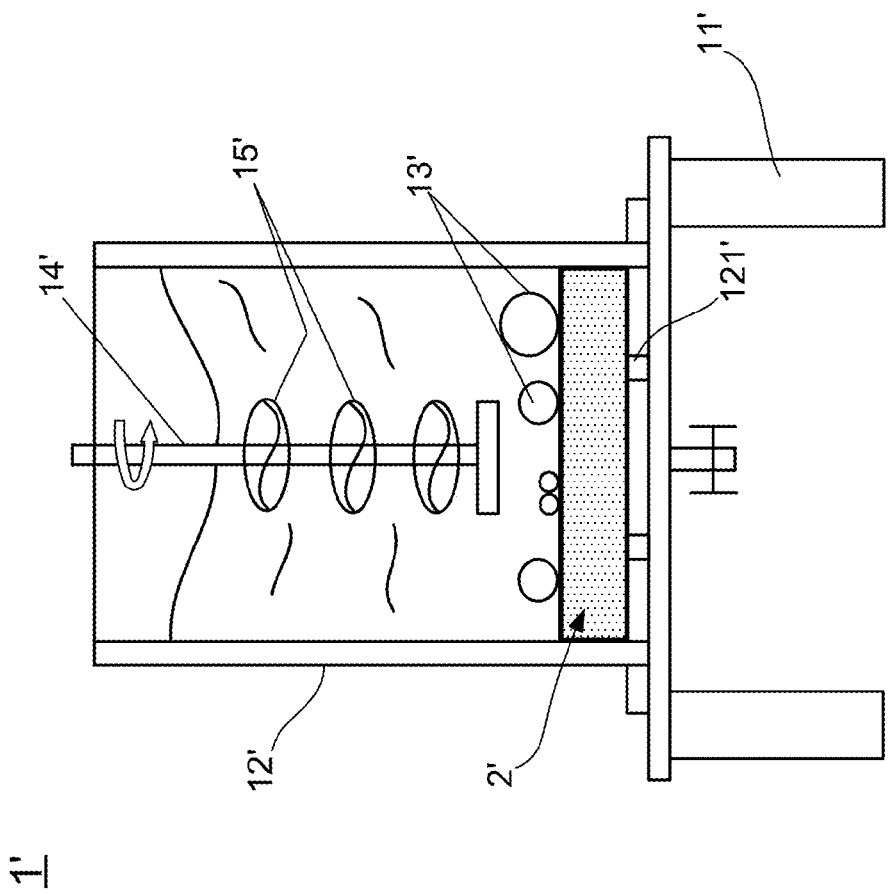
FIG. 1 is a cross-sectional view of a conventional C1138 abrasion testing machine.
Figure 2:
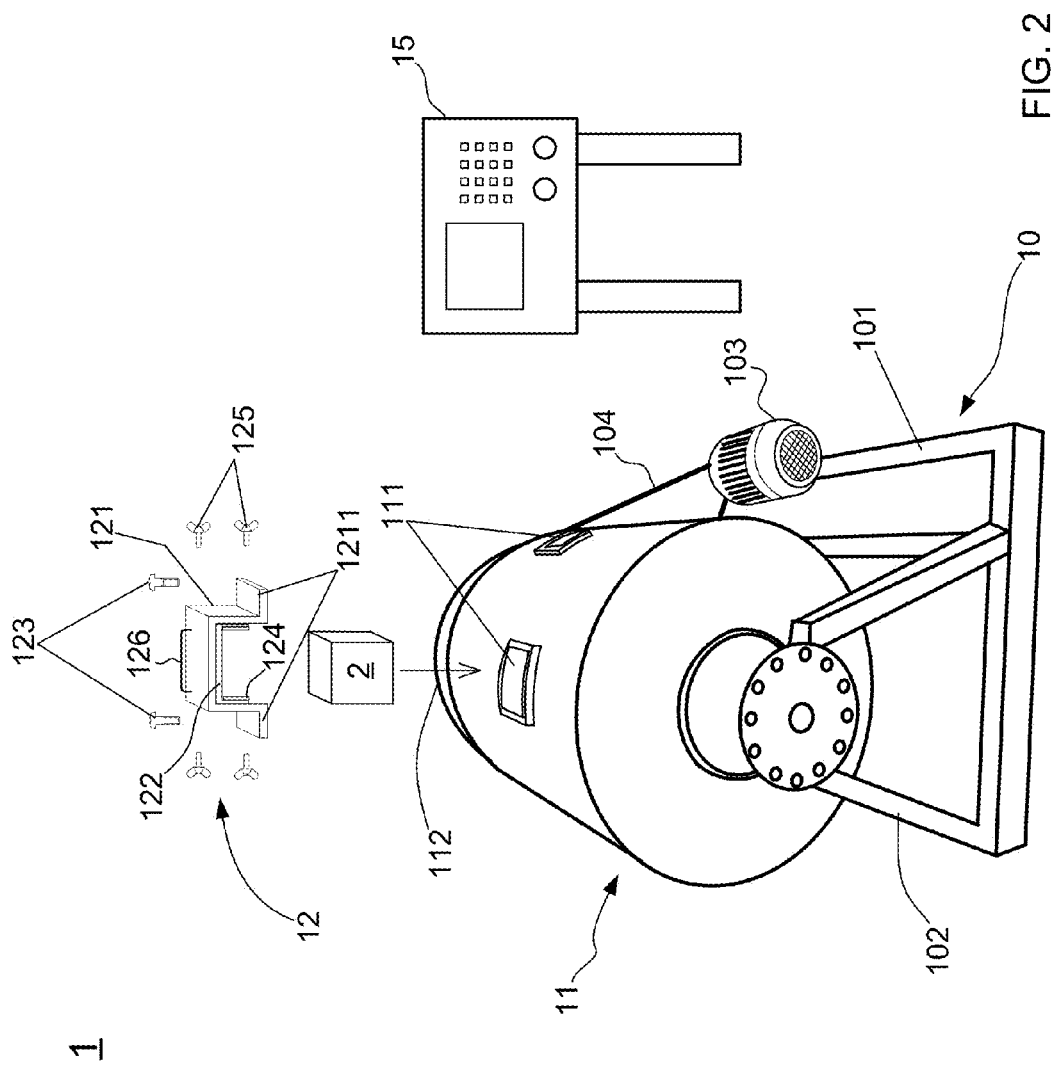
FIG. 2 is a stereo diagram of a rotary-drum hydraulic-impact abrasion testing machine according to the present invention.

Please refer to FIG. 2, which illustrates a stereo diagram of a rotary-drum hydraulic-impact abrasion testing machine according to the present invention. In the present invention, as shown in FIG. 2, the rotary-drum hydraulic-impact abrasion testing machine 1 is used for processing an abrasion test and a damage simulation for a plurality of hydraulics structure samples 2, and includes: a rotary-drum supporting framework 10, a rotary-drum 11 and a plurality of sample fixing assemblies 12. The rotary-drum supporting framework 10 consists of a bottom portion 101 and two supporting portions 102, wherein the bottom portion 101 of the rotary-drum supporting framework 10 is disposed with a motor 103. Herein, the hydraulics structure sample 2 means the sample of concrete hydraulics structure.

Continuously Referring to FIG. 2, there are a plurality of sample openings 111 disposed on the side walls of the rotary-drum 11, used for disposing and accommodating the hydraulics structure samples 2. In addition, two driving shafts (not shown) are respectively set on the top and the bottom of the rotary-drum 11, so that the rotary-drum 11 can be disposed on the rotary-drum supporting framework 10 by way of connecting the two driving shafts to the two supporting portions 102. Moreover, the rotary-drum 11 further includes a driving disc 112, which is connected to the driving shaft on the top of the rotary-drum 11. As shown in FIG. 2, one end of the driving belt 104 covers the driving disc 112 and another end the driving belt 104 is stuck the driving axis of the motor 103, therefore the rotary-drum 11 can be driven to rotate via the driving belt 104 when the motor 103 is operated.

Figure 3:
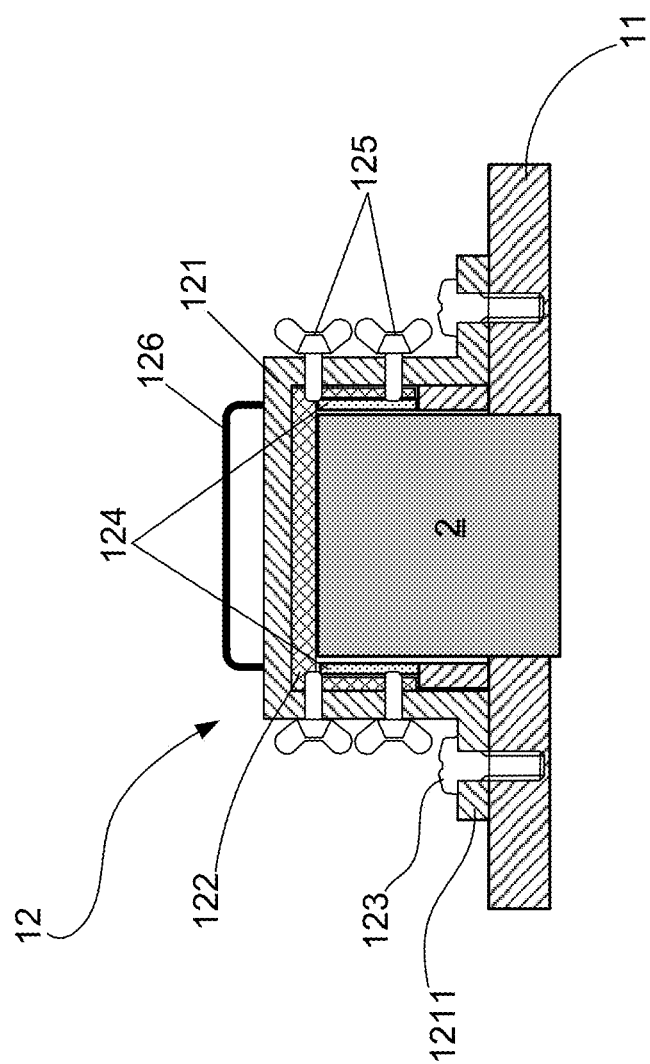
FIG. 3 is a side view of a sample fixing assembly of the rotary-drum hydraulic-impact abrasion testing machine.

The sample fixing assemblies 12 are used for respectively fixing the hydraulics structure samples 2 in the sample openings 111. Please refer to FIG. 2 again and continuously refer to FIG. 3, which illustrates a side view of a sample fixing assembly of the rotary-drum hydraulic-impact abrasion testing machine. As shown in FIG. 2, the sample fixing assemblies 12 are capable of fixing the hydraulics structure samples 2 on the side walls of the rotary-drum 11 after the hydraulics structure samples 2 are put into the sample openings 111. And as shown in FIG. 3, each sample fixing assembly 12 consists of: a housing 1214, a first spacer 122, a plurality of first studs 123, a plurality of second spacers 124, a plurality of second studs 125, and a handle 126, wherein the housing 121 is used for partially accommodating and sheltering the hydraulics structure sample 2, and the housing 121 has two fixing portions 1211. The first spacer 122 is made of metal, which is disposed between the housing 121 and the hydraulics structure sample 2 for being a cushioning. The first studs 123 are used for screwing through the fixing portions 1211, so as to secure the housing 121 accommodated with the hydraulics structure sample 2 on the roller body of the rotary-drum 11.

In the present invention, as shown in FIG. 3, the second spacers 124 are made of rubber, plastics or silica, which are disposed on the rear side, left side and right side of the hydraulics structure sample 2. To detailedly introduce the second spacer 124, each second spacer 124 has a specific thickness adjustable according to different lengths and widths of the hydraulics structure sample 2, such that all of the hydraulics structure samples 2 with distinct lengths and widths are able to be partially accommodated in the housing 121.

Figure 4:
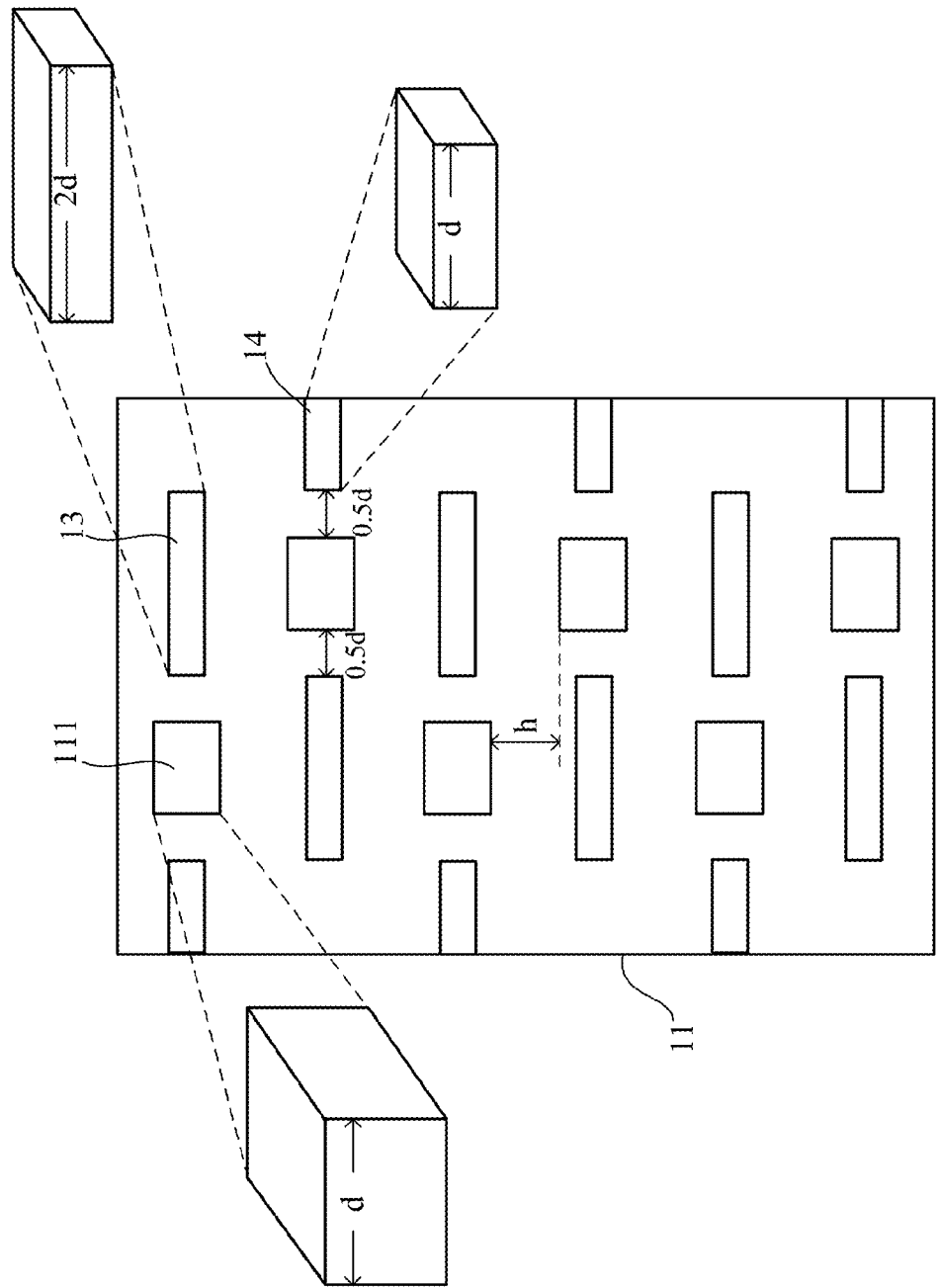
FIG. 4 is a plane-development view of the inner side wall of a rotary-drum of the rotary-drum hydraulic-impact abrasion testing machine.

Please refer to FIG. 4, there is shown a plane-development view of the inner side wall of the rotary-drum. In FIG. 4, the circular inner side wall of the rotary-drum 11 is expanded to a plane inner side wall for clearly explaining the structure thereof. As shown in FIG. 4, the inner side wall of the rotary-drum 11 is provided with a plurality of long blocking plates 13 and short blocking plates 14, wherein each of the long blocking plates 13 and the short blocking plates 14 are alternatively disposed around each of the sample openings 111, and the blocking plates 13, 14 are axially-extended in parallel around each of the sample openings 111 in the rotary-drum 11. In the present invention, for increasing the accuracy of the abrasion test and the damage simulation of the hydraulics structure samples 2, the length of the long blocking plate 13 is designed to double of the short blocking plate's 14, and the length of the short blocking plate 14 is equal to the length of the sample opening 111. As shown in figure, if "d" means the length of the sample opening 111, "d" and "2 d" means the length of the short blocking plate 14 and the long blocking plate 13, respectively.

Inheriting to above descriptions, besides the demand on the length of the long blocking plates 13 and the short blocking plates 14, the distance between the long blocking plates 13 and the sample opening 111 is half of the length of the sample opening 111; And similarly, the distance between the short blocking plates 14 and the sample opening 111 is half of the length of the sample opening 111. So that, as shown in FIG. 4, if "d" means the length of the sample opening 111, then the "0.5 d" means the distance between the long blocking plates 13 and the sample opening 111 as well as the distance between the short blocking plates 14 and the sample opening 111. In addition, there is a specific vertical distance "h" between any adjacent sample openings 111.

Figure 5A:
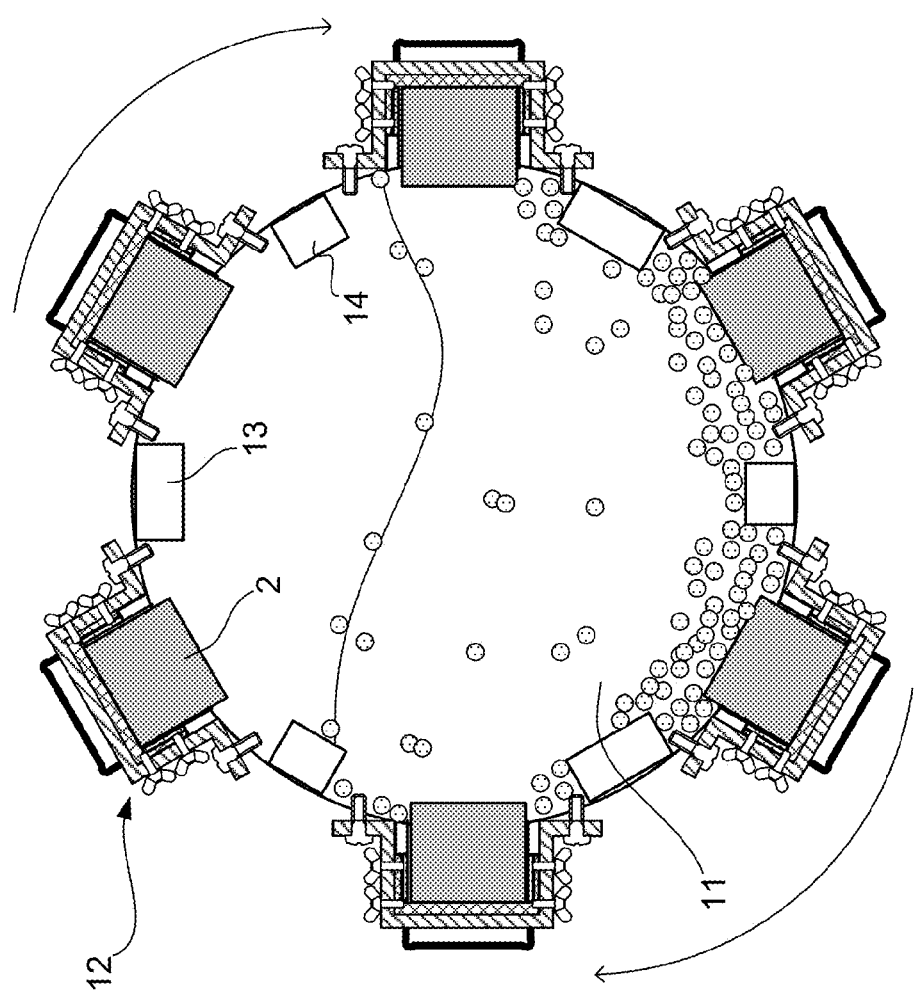
FIG. 5A and FIG. 5B are application illustrations of the rotary-drum hydraulic-impact abrasion testing machine according to the present invention.
Figure 5B:
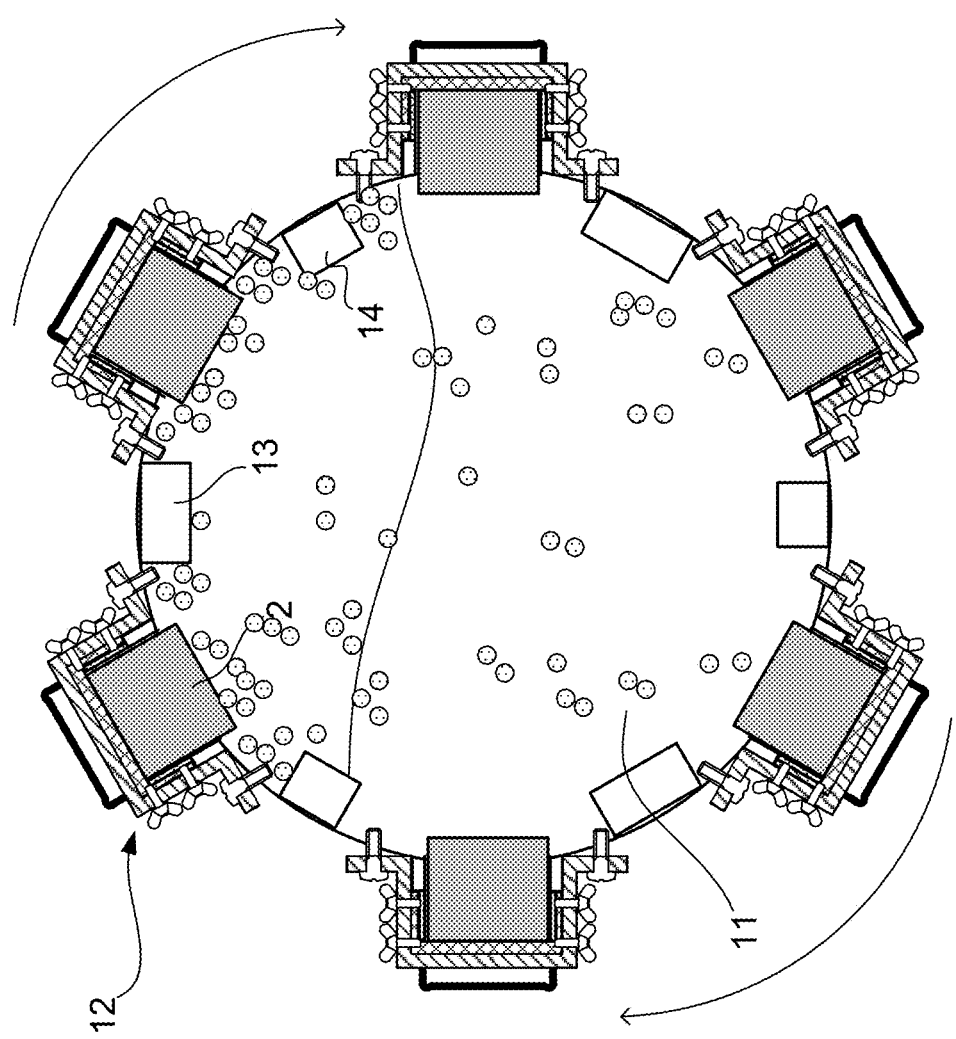

Through above descriptions, the basic constitutions of the rotary-drum hydraulic-impact abrasion testing machine of the present invention have been clearly introduced; then, the way for using this rotary-drum hydraulic-impact abrasion testing machine to process the abrasion test and the damage simulation for the hydraulics structure samples will sequentially be described. Please refer to FIG. 5A and FIG. 5B, there are shown application illustrations of the rotary-drum hydraulic-impact abrasion testing machine according to the present invention. As shown in FIG. 5A, when processing the abrasion test, the hydraulics structure samples 2 are put into the sample openings 111 and fixed on the roller body of the rotary-drum 11 through the sample fixing assemblies 12. Then, the water containing sand is injected into the rotary-drum 11, and the motor 103 is next operated for driving the rotary-drum 11 to rotate. As shown in FIG. 5A, when the rotary-drum 11 is driven in a low speed rotating, the water containing sand would down to the bottom of the rotary-drum 11 due to the attraction of gravity, meanwhile the hydraulics structure samples 2 located in the bottom of the rotary-drum 11 would contact with the water containing sand and be abraded. In addition, as shown in FIG. 5B, when rotary-drum 11 is driven in a high speed rotating, the water containing sand would fall down after colliding with the long blocking plates 13 and the short blocking plates 14, and then impact the hydraulics structure samples 2.

Inheriting to above descriptions, the abrasion test and the damage simulation for the hydraulics structure samples 2 can also be processed by injecting the water containing steel ball into the rotary-drum 11, and then driving the rotary-drum 11 to rotate by the motor 103. Moreover, the machine operator is able to set the rolling cycles and the rolling speed of the rotary-drum 11 via the controlling device 15 shown in FIG. 2, therefore not only the accuracy of the abrasion test can be effectively controlled, but also the abrasion and the (top and side) surfaces damage simulation of the hydraulics structure samples 2 are precisely verified.

Thus, the above descriptions have been clearly and completely introduced the rotary-drum hydraulic-impact abrasion testing machine of the present invention. In summary, the present invention has the following advantages:

1. Through the particularly design of the sample openings, the sample fixing assemblies, the long blocking plates, and the short blocking plates, the rotary-drum hydraulic-impact abrasion testing machine of the present invention can be used to accurately process the abrasion test and the damage simulation for the hydraulics structure samples.
2. Inheriting to above point 1, in addition, by controlling the rolling speed of the rotary-drum, the rotary-drum hydraulic-impact abrasion testing machine of the present invention can be used for processing the abrasion and the (top and side) surfaces damage of the hydraulics structure samples through injecting the water containing sand or the water containing steel ball into the rotary-drum and then driving the rotary-drum to rotate by the motor, therefore the various natural erosions of the hydraulics structure samples can be verified and simulated.
3. Moreover, in the rotary-drum hydraulic-impact abrasion testing machine, each second spacer has a specific thickness, and the specific thickness can be adjusted according to different lengths and widths of the hydraulics structure sample, such that all of the hydraulics structure samples having distinct lengths and widths are able to be partially accommodated in the housing, and all these hydraulics structure samples having distinct lengths and widths can be executed the abrasion test and the damage simulation; That is extremely helpful to the optimization design of the hydraulics structures.

The above description is made on embodiments of the present invention. However, the embodiments are not intended to limit scope of the present invention, and all equivalent implementations or alterations within the spirit of the present invention still fall within the scope of the present invention.

We claim:

1. A rotary-drum hydraulic-impact abrasion testing machine, comprising:
    a rotary-drum supporting framework;
    a rotary-drum, disposed on the rotary-drum supporting framework, provided with at least one sample opening for accommodating at least one hydraulics structure sample; and
    at least one sample fixing assembly used for fixing the hydraulics structure sample in the sample opening;
    wherein the inner side walls of the rotary-drum are provided with a plurality of blocking plates axially-extended in parallel around each of the sample openings, in the rotary-drum.
2. The rotary-drum hydraulic-impact abrasion testing machine of claim 1, wherein the blocking plates comprises a plurality of long blocking plates and short blocking plates, in which each of the long blocking plates and the short blocking plates are alternatively disposed around each of the sample openings, so as to make the long blocking plates and short blocking plates surround all sample openings.
3. The rotary-drum hydraulic-impact abrasion testing machine of claim 2, wherein the distance between the long blocking plates and the sample opening is half of the length of the sample opening.
4. The rotary-drum hydraulic-impact abrasion testing machine of claim 2, wherein the distance between the short blocking plates and the sample opening is half of the length of the sample opening.
5. The rotary-drum hydraulic-impact abrasion testing machine of claim 1, wherein the rotary-drum supporting framework comprises a bottom portion and at least one supporting portion, in which a motor is disposed on the bottom portion for driving the rotary-drum disposed on the supporting portion.
6. The rotary-drum hydraulic-impact abrasion testing machine of claim 1, wherein the sample fixing assembly comprises:
    a housing for partially accommodating and sheltering the hydraulics structure sample, and the housing having at least one fixing portion;
    a first spacer disposed between the housing and the hydraulics structure sample for cushioning; and
    a plurality of first studs for screwing through the fixing portions, so as to secure the housing accommodated with the hydraulics structure sample on the roller body of the rotary-drum.
7. The rotary-drum hydraulic-impact abrasion testing machine of claim 6, wherein the sample fixing assembly comprises:
    a plurality of second spacers disposed between the first spacer and the hydraulics structure sample, wherein the second spacer has a specific thickness adjustable according to different lengths and widths of the hydraulics structure sample, such that all of the hydraulics structure samples with distinct lengths and widths are able to be partially accommodated in the housing;
    a plurality of second studs, being used for screwing into the housing from the outer side walls of the housing, so as to fix the hydraulics structure sample partially accommodated in the housing; and
    a handle connected to the housing.
8. The rotary-drum hydraulic-impact abrasion testing machine of claim 1, which is able to process an abrasion test and a damage simulation for the hydraulics structure sample by injecting water containing sand or water containing steel balls into the rotary-drum, and then driving the rotary-drum to rotate with a motor.
9. The rotary-drum hydraulic-impact abrasion testing machine of claim 1, wherein a specific vertical distance is formed between two adjacent sample openings.
10. The rotary-drum hydraulic-impact abrasion testing machine of claim 1, wherein the rotary-drum further comprises a driving disc, a driving belt and a driving shaft connected to the driving disc, in which one end of the driving belt is stuck to the driving disc, and another end the driving belt is stuck to the driving axis of a motor.

* * * * *